United States Patent [19]

Mathison et al.

[11] 3,963,723
[45] June 15, 1976

[54] CYCLOPENTANO (H) OR (F) 1,2,3,4-TETRAHYDROISOQUINOLINES

[75] Inventors: Ian William Mathison; William Ebenezer Solomons, both of Memphis, Tenn.; Raymond Henry Jones, Northport, N.Y.

[73] Assignee: Marion Laboratories, Inc., Kansas City, Mo.

[22] Filed: Mar. 28, 1974

[21] Appl. No.: 455,574

[52] U.S. Cl. .................. 260/286 R; 260/283 SY; 260/289 C; 260/566 R; 260/570.8 R; 260/613 D; 424/258
[51] Int. Cl.² ..................................... C07D 217/00
[58] Field of Search ...... 260/289 R, 289 C, 283 SY, 260/570.8 R, 566 R, 613 D, 286 CF

[56] References Cited
UNITED STATES PATENTS
3,541,158  11/1970  Shulgin ........................... 260/613 D

FOREIGN PATENTS OR APPLICATIONS
273,204  8/1970  U.S.S.R. ........................ 260/289 C

OTHER PUBLICATIONS

Brown et al., "J. Chem. Soc.," pp. 4295–4298 (1961).

*Primary Examiner*—Raymond V. Rush
*Assistant Examiner*—D. B. Springer
*Attorney, Agent, or Firm*—Merriam, Marshall, Shapiro & Klose

[57] ABSTRACT

Provided are novel cyclopentano-1,2,3,4-tetrahydroisoquinolines of the formula

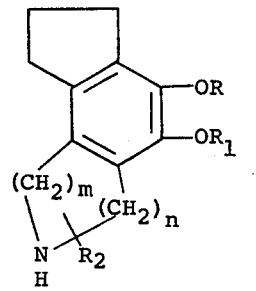

wherein R and $R_1$ are the same or different lower alkyl groups, $R_2$ is hydrogen or a lower alkyl group, $m$ is an integer from 1 to 2, $n$ is an integer from 1 to 2 and $m + n$ equals 3, and acid addition salts thereof, processes for making the compounds and pharmaceutical compositions containing one or more of the compounds useful as hypotensive agents. Also provided are intermediates of the formula

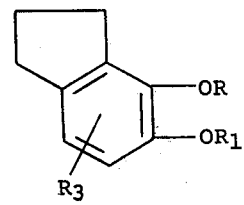

wherein R and $R_1$ are the same or different lower alkyl groups and $R_3$ is hydrogen, CHO—,

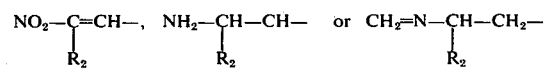

wherein $R_2$ is hydrogen or a lower alkyl group.

9 Claims, No Drawings

CYCLOPENTANO (H) OR (F) 1,2,3,4-TETRAHYDROISOQUINOLINES

This invention relates to novel chemical compounds and their production. More particularly, this invention provides novel tetrahydroisoquinolines, processes for producing the compounds, novel intermediates useful in making the compounds, and novel pharmaceutical compositions containing the compounds useful for effecting desirable pharmacological activity in animals.

According to one aspect of the subject invention there is provided novel cyclopentano-1,2,3,4-tetrahydroisoquinolines of the formula:

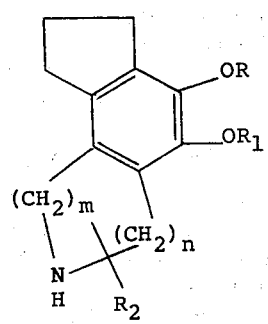

Formula 1 wherein R and $R_1$ are the same or different lower alkyl groups containing 1 to 6 carbon atoms such as methyl, ethyl, propyl, isopropyl, butyl, pentyl and hexyl, $R_2$ is hydrogen or a lower alkyl group having 1 to 6 carbon atoms such as methyl or ethyl, m is an integer from 1 to 2, n is an integer from 1 to 2 and $m + n$ equals 3.

when m is 1 and n is 2 in Formula 1 the compounds can be represented by Formula 2:

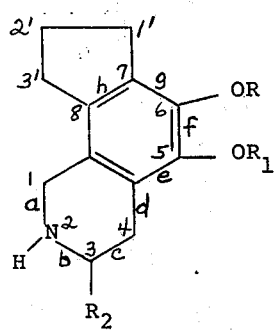

Formula 2 wherein R, $R_1$ and $R_2$ have the significance previously assigned, and they are named 5,6-dialkoxy-cyclopentano[h]1,2,3,4-tetrahydroisoquinoline.

When m is 2 and n is 1 in Formula 1 the compounds can be represented by Formula 3:

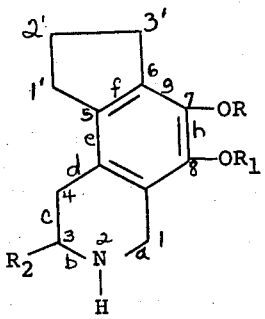

Formula 3 wherein R, $R_1$ and $R_2$ have the significance previously assigned, and they are named 7,8-dialkoxy-cyclopentano[f]1,2,3,4-tetrahydroisoquinoline.

To prepare the compounds of this invention, intermediate indanaldehydes of Formula 4 are first prepared:

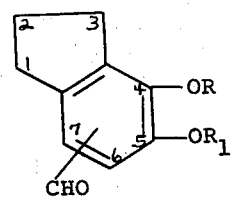

Formula 4 in which the —CHO or aldehyde group, is in the 6 or 7-position.

The intermediate 6- or 7-indanaldehydes of Formula 4 can be prepared by reducing a 4,5-dialkoxy-1-indanone to 4,5-dialkoxyindane and then converting that compound by means of a Friedel-Crafts reaction to a mixture of 4,5-dialkoxy-6-indanaldehyde and 4,5-dialkoxy-7-indanaldehyde. This series of reactions can be represented as follows:

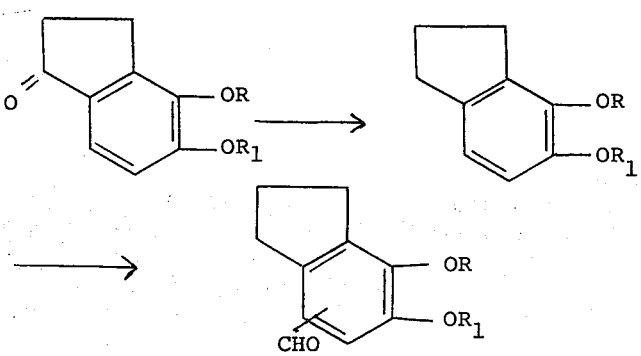

wherein R and $R_1$ have the previously assigned significance.

Among the starting materials which can be used in the described sequence of reactions are 4,5-dimethoxy-1-indanone, 4,5-diethoxy-1-indanone, 4,5-dipropoxy-1-indanone and 4-methoxy-5-ethoxy-1-indanone. The publication of John Koo in J. Am. Chem. Soc., 75, 1891 (1953) discloses 4,5-dimethoxy-1-indanone. Other similar compounds, such as those just named, can be prepared by the procedure disclosed therein.

Reduction of the 4,5-dialkoxy-1-indanone can be readily achieved catalytically using hydrogen and a suitable catalyst such as palladium. The hydrogenation is effected by placing the starting material in glacial acetic acid containing the catalyst and a small amount of concentrated hydrochloric acid. The hydrogenation proceeds readily at room temperature using a hydrogen pressure of about 25 to 100 psig. After hydrogen uptake has ceased the product can be recovered from the reaction mixture by conventional methods.

Some 4,5-dialkoxyindanes which can be produced as described are 4,5-dimethoxyindane, 4,5-diethoxyindane, 4,5-dipropoxyindane, 4,5-diisopropoxyindane, 4,5-dibutoxyindane and 4-methoxy-5-ethoxyindane.

Formylation of a 4,5-dialkoxyindan according to the method of Alfred Rieche et al. in Chem. Ber., 93, 88 (1960) using a Friedel-Crafts catalyst such as stannic tetrachloride aluminum trichloride or titanium tetrachloride and α,α-dichloromethyl methyl ether followed by water leads to the production of a mixture containing 4,5-dialkoxy-6-indanaldehyde and 4,5-dialkoxy-7-indanaldehyde. The presence of a mixture of isomeric aldehydes is shown by glc. A mixture of 4,5-dimethoxy-6- and -7-indanaldehydes formed by the described procedure contains about 75% of the 7-formyl and 25% of the 6-formyl isomers. Obviously, the presence of other alkoxy groups than the methoxy group could lead to different amounts of the isomers in the resulting mixture.

The isomeric mixture of aldehydes obtained by the described process is generally a liquid. Residual amounts of solvent are removed from the liquid by distillation following which the product is distilled under high vacuum to give a pure liquid mixture. Upon cooling, one of the isomeric aldehydes crystallizes from the liquid and is removed by filtration. Thus, 4,5-dimethoxy-7-indanaldehyde crystallizes and leaves a liquid which is primarily 4,5-dimethoxy-6-indanaldehyde. Fractional distillation of the liquid gives the pure 6-formyl isomer.

Some of the separated purified aldehydes which can be prepared by the described method are:
4,5-dimethoxy-6-indanaldehyde,
4,5-dimethoxy-7-indanaldehyde,
4,5-diethoxy-6-indanaldehyde,
4,5-diethoxy-7-indanaldehyde,
4,5-dipropoxy-6-indanaldehyde,
4,5-dipropoxy-7-indanaldehyde,
4-methoxy-5-ethoxy-6-indanaldehyde, and
4-methoxy-5-ethoxy-7-indanaldehyde.

Preparation of Formula 2 Compounds

The 5,6-dialkoxy-cyclopentano[h]1,2,3,4-tetrahydroisoquinolines of Formula 2 are prepared from the 4,5-dialkoxy-6-indanaldehydes by reacting the aldehyde with a 1-nitroalkane to produce a 4,5-dialkoxy-6-nitrovinylindane, chemically reducing the nitrovinyl compound to the corresponding aminoalkyl compound, reacting the resulting amine with formaldehyde to produce a Schiff's base and then treating the Schiff's base with acid to effect a Pictet-Spengler acid catalyzed ring closure. This series of reactions can be represented as follows:

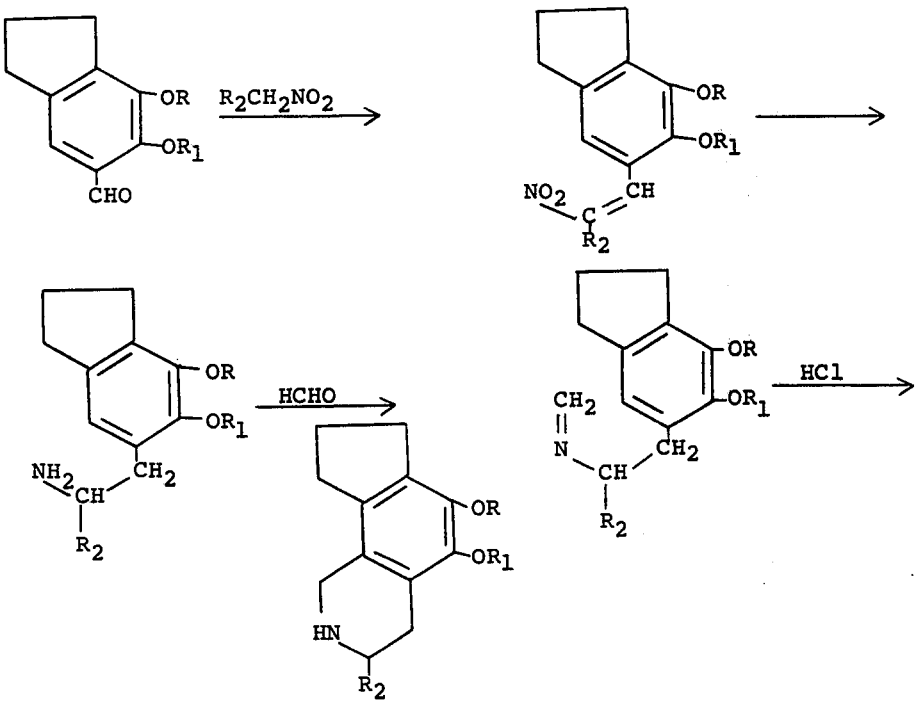

wherein R, $R_1$ and $R_2$ have the previously assigned significance.

In effecting the first step of this series of reactions, nitromethane, nitroethane, 1-nitropropane and other such 1-nitroalkanes can be used.

Condensation of the 4,5-dialkoxy-6-indanaldehyde with the nitroalkane can be readily effected by procedures discussed in Gairaud et al., J. Org. Chem., 18, 1

(1953) and particularly by the use of ammonium acetate in glacial acetic acid at an elevated temperature. After cooling the reaction mixture, the desired 4,5-dialkoxy-6-nitrovinylindane crystallizes from solution and is separated by filtration.

By following the described procedure there is obtained 4,5-dimethoxy-6-nitrovinylindane, 4,5-dimethoxy-6-(2-nitro-2-methylvinyl)indane, 4,5-dimethoxy-6-(2-nitro-2-ethylvinyl)indane, 4,5-diethoxy-6-nitrovinylindane, 4,5-dipropoxy-6-nitrovinylindane and 4-methoxy-5-ethoxy-6-nitrovinylindane.

The 4,5-dialkoxy-6-nitrovinylindanes are readily reduced chemically by means of lithium aluminum hydride in dry ether according to the method of Marchant et al., J. Chem. Soc. 327 (1956) to produce the desired 4,5-dialkoxy-6-aminoethylindanes. Some of the compounds which are produced in this way are 4,5-dimethoxy-6-aminoethylindane, 4,5-diethoxy-6-(2-aminopropyl)indane, 4,5-dipropoxy-6-(2-aminobutyl)indane and 4-methoxy-5-ethoxy-6-aminoethylindane.

Representative cyclopentano[h]1,2,3,4-tetrahydroisoquinolines which are produced as described are 5,6-dimethoxy-cyclopentano[h]1,2,3,4-tetrahydroisoquinoline, 5,6-diethoxy-cyclopentano[h]1,2,3,4-tetrahydroisoquinoline, 5,6-dipropoxy-cyclopentano[h]1,2,3,4-tetrahydroisoquinoline and 5-methoxy-6-ethoxy-cyclopentano[h]1,2,3,4-tetrahydroisoquinoline.

Preparation of Formula 3 Compounds

The 7,8-dialkoxy-cyclopentano[f]1,2,3,4-tetrahydroisoquinolines of Formula 3 are prepared from the 4,5-dialkoxy-7-indanaldehydes by reacting the aldehyde with a 1-nitroalkane to produce a 4,5-dialkoxy-7-nitrovinylindane, chemically reducing the nitrovinyl compound to the corresponding aminoalkyl compound, reacting the resulting amine with formaldehyde to produce a Schiff's base and then treating the Schiff's base with acid to effect a Pictet-Spengler acid catalyzed ring closure. This series of reactions can be represented as follows:

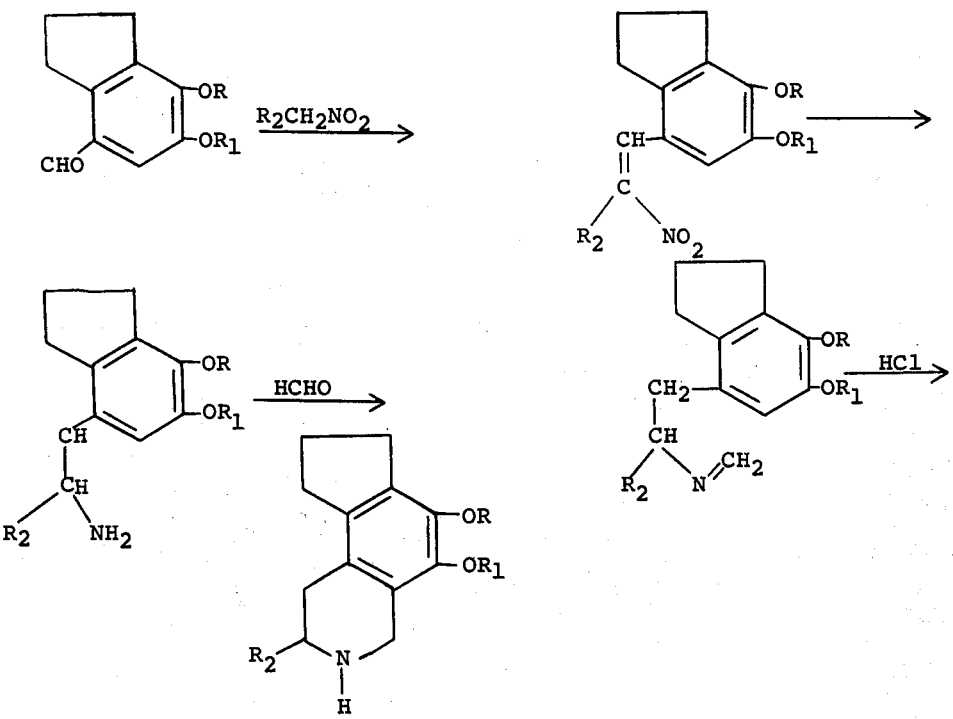

wherein R, $R_1$ and $R_2$ have the previously assigned significance.

In effecting the first step of this series of reactions, nitromethane, nitroethane, 1-nitropropane and other such 1-nitroalkanes can be used.

Condensation of the 4,5-dialkoxy-7-indanaldehyde with the nitroalkane can be readily effected by procedures discussed in Gairaud et al., J. Org. Chem. 18, 1 (1953) and particularly by the use of ammonium acetate in glacial acetic acid at an elevated temperature.

By following the described procedure there is obtained 4,5-dimethoxy-7-nitrovinylindane, 4,5-dimethoxy-7-(2-nitro-2-methylvinyl)indane, 4,5-dimethoxy-7-(2-nitro-2-ethylvinyl)indane, 4,5-diethoxy-7-nitrovinylindane, 4,5-dipropoxy-7-nitrovinylindane and 4-methoxy-5-ethoxy-7-nitrovinylindane.

The 4,5-dialkoxy-6-aminoethylindanes are converted to the Schiff's bases by reaction with formaldehyde using conventional reaction conditions for preparing Schiff's bases. Some of the compounds so produced are N-methylidene-4,5-dimethoxy-6-(2-aminoethyl)indane, N-methylidene-4,5-diethoxy-6-(2-aminopropyl)indane, N-methylidene-4,5-dipropoxy-6-(2-aminobutyl)indane and N-methylidene-4-methoxy-5-ethoxy-6-(2-aminoethyl)indane.

The described Schiff's bases are readily cyclized in aqueous acid, such as 23% hydrochloric acid, at a moderately elevated temperature of about 40° to 75°C., to the cyclopentano[h]1,2,3,4-tetrahydroisoquinolines. The product is readily recovered by evaporation of the solvent and acid.

The 4,5-dialkoxy-7-nitrovinylindanes are readily reduced chemically by means of lithium aluminum hydride in dry ether according to the method of Marchant et al., J. Chem. Soc., 327 (1956) to produce the desired 4,5-dialkoxy-7-aminoethylindanes. Some of the compounds which are produced in this way are 4,5-dimethoxy-7-aminoethylindane, 4,5-diethoxy-7-(2-aminopropyl)indane, 4,5-dipropoxy-7-(2-aminobutyl)indane and 4-methoxy-5-ethoxy-7-aminoethylindane.

The 4,5-dialkoxy-7-aminoethylindanes are converted to the Schiff's bases by reaction with formaldehyde using conventional reaction conditions for preparing Schiff's bases. Some of the compounds so produced are N-methylidene-4,5-dimethoxy-7-(2-aminoethyl)indane, N-methylidene-4,5-diethoxy-7-(2-aminopropyl)indane, N-methylidene- 4,5-dipropoxy-7-(2-aminobutyl)indane and N-methylidene-4-methoxy-5-ethoxy-7-(2-aminoethyl)indane.

The described Schiff's bases are readily cyclized in aqueous acid, such as 23% hydrochloric acid, at a moderately elevated temperature of about 40° to 75°C., to the cyclopentano [f]1,2,3,4-tetrahydroisoquinolines. The product is readily recovered by evaporation of the solvent and acid.

Representative cyclopentano [f]1,2,3,4-tetrahydroisoquinolines which are produced as described are 7,8-dimethoxy-cyclopentano [f]1,2,3,4-tetrahydroisoquinoline, 7,8-diethoxy-cyclopentano [f]1,2,3,4-tetrahydroisoquinoline, 7,8-dipropoxy-cyclopentano [f]1,2,3,4-tetrahydroisoquinoline and 7-methoxy-8-ethoxy-cyclopentano [f]1,2,3,4-tetrahydroisoquinoline.

The 5,6-dialkoxy-cyclopentano [h]1,2,3,4-tetrahydroisoquinolines and 7,8-dialkoxy-cyclopentano [f]1,2,3,4 -tetrahydroisoquinolines, being amines, can be converted to acid addition salts by contacting the amines with a suitable inorganic acid such as hydrochloric acid, sulfuric acid, phosphoric acid and hydrobromic acid or an organic acid such as citric acid, acetic acid, formic acid, malic acid, fumaric acid, succinic acid, benzoic acid and tartaric acid.

The 5,6-dialkoxy-cyclopentano [h]1,2,3,4-tetrahydroisoquinolines and the 7,8-dialkoxy-cyclopentano [f]1,2,3,4-tetrahydroisoquinolines are useful as neutralizing agents since they are bases which form salts with acids.

According to a second aspect of the invention, the 5,6-dialkoxy-cyclopentano [h]1,2,3,4-tetrahydroisoquinolines and the 7,8-dialkoxy-cyclopentano [f]1,2,3,4-tetrahydroisoquinolines are also useful pharmaceutically. These compounds when administered to animals intraperitoneally or orally exert an anti-hypertensive effect. The compounds thus can be used to reduce blood pressure.

The amount of active ingredient administered may be varied; however, it is necessary that the amount of active ingredient be such that a suitable dosage is given. The selected dosage depends upon the desired therapeutic effect and on the duration of treatment. Dosages of from 0.1 to 25 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg. of active agent.

A typical tablet can have the composition:

|  | Mg |
|---|---|
| Active agent (1) | 10 |
| Starch U.S.P. | 57 |
| Lactose U.S.P. | 73 |
| Talc. U.S.P. | 9 |
| Stearic acid | 12 |

(1) 7,8-dimethoxy-cyclopentano[f]1,2,3,4-tetrahydro-isoquinoline HCl or 5,6-dimethoxy-cyclopentano[h]1,2,3,4-tetrahydroisoquinoline HCl The compounds of Formulas 2 and 3 exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like containing diluents commonly used in the art, such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

5,6-dimethoxy-cyclopentano [h]1,2,3,4-tetrahydroisoquinoline base has an $ALD_{50}$ in mice of 25 mg/kg intraperitoneally. When administered at 5 to 10 mg/kg ip to hypertensive rats a significant lowering of systolic blood pressure results although the 10 mg/kg dose heralded approach to a toxic level. In the anesthetized normotensive dog, a dose of 2–4 mg/kg iv lowered the mean blood pressure 71% with a 50% return in pressure after 6 minutes. 7,8-dimethoxy-cyclopentano [f]1,2,3,4-tetrahydroisoquinoline HCl has an $ALD_{50}$ in mice of 79-89 mg/kg intraperitoneally. When administered at 10 to 20 mg/kg ip to hypertensive rats significant lowering of systolic blood pressure results. In the anesthetized normotensive dog, a dose of 2 to 6.6 mg/kg iv lowered the mean blood pressure 48% with a 50% return in pressure after 11 minutes.

The following examples are presented to further illustrate the invention.

EXAMPLE 1

4,5-Dimethoxyindane

A mixture of 52.6 g (0.275 mole) of 4,5-dimethoxy-1-indanone, 3.00 g of 5% Pd/C, 100 ml of glacial acetic acid and 20 drops of conc. HCl was hydrogenated at 45 psi and room temperature until hydrogen uptake ceased. Following filtration of the used catalyst, two methods were used to work up the reaction.

A. The acid was neutralized with dilute sodium hydroxide and the product extracted from the aqueous phase with ether. The ether was removed by distillation and crude 4,5-dimethoxyindane was distilled under reduced pressure, b.p. 133°–135°C (15 mm) yielding 42.0 g (86.4%) of clear liquid. Infrared analysis showed the absence of carbonyl absorption.

B. Most of the acetic acid was removed on the rotary evaporator and the remaining liquid was distilled as before giving 4,5-dimethoxyindane with no significant difference in yield from that obtained in A.

EXAMPLE 2

4,5-Dimethoxy-7-indanaldehyde

To a solution of 10.0 g (0.056 mole) of 4,5-dimethoxyindane, 24.0 g (0.126 mole) of titanium tetrachloride and 104 ml of $CH_2Cl_2$ in a 250 ml 3-necked flask fitted with a thermometer and condenser and magnetically stirred, 11.0 g (0.096 mole) of $\alpha,\alpha$-dichloromethyl methyl ether was added rapidly dropwise at 0°C. Hydrogen chloride gas was liberated during the course of the reaction. After vigorous evolution of HCl had subsided, the reaction solution was allowed to slowly warm to room temperature and it was stirred for 1 to 2 hours. The solution was refluxed for 6 hours, cooled and the reaction mixture was poured over 200 ml of ice and water (ether and salt were added at this point to increase the volume of the organic phase, to invert the two layers and to break emulsions). The organic phase was washed with 2 × 100 ml of 8% NaHCO$_3$ solution, 1 × 100 ml of water and dried over Na$_2$SO$_4$. After removal of the solvent by distillation, the mixture of aldehyde isomers was distilled under high vacuum (b.p. 115°–126°C; 0.28 mm) giving 10.2 g of the 6- and 7-position aldehydes (88%). The 7-position aldehyde which crystallized from the liquid was filtered. This process was repeated several times by seeding the filtrate followed by cooling. Gas chromatography showed the white crystalline solid 4,5-dimethoxy-7-indanaldehyde to be one component of the two component mixture. In this way 4.24 g of white solid was obtained, m.p. 41°–44°C, yield 38.5%. Anal. Calcd. for $C_{12}H_{14}O_3$: C, 69.88; H, 6.84. Found: C, 70.03; H, 6.66.

EXAMPLE 3

4,5-Dimethoxy-7-nitrovinylindane

To a 100 ml 3-necked round bottom flask fitted with a condenser and thermometer and magnetically stirred, was added 12.97 g (0.063 mole) of 4,5-dimethoxy-7-indanaldehyde, 3.00 g (0.039 mole) of ammonium acetate, 13.0 ml (0.292 mole) of $CH_3NO_2$ and 40 ml of glacial acetic acid. This mixture was heated for 1 to 2 hours at 112°C. As the reaction solution began to cool the entire solution solidified. After cooling in an ice bath and removing the solvent by filtration, the solid 4,5-dimethoxy-7-nitrovinylindane was washed with a small volume of acetic acid giving fine yellow needles (9.55 g) after thorough drying. The filtrate was poured into 300 ml of ice and water from which precipitated a slightly gummy, yellow-brown solid. This gave an additional 1.43 g of crystalline solid after drying and crystallizing from methanol giving a total yield of 10.98 g (70%). An analytical sample melted at 128°–130°C. Anal. Calcd. For $C_{13}H_{15}NO_4$: C, 62.64; H, 6.06; N, 5.62. Found: C, 62.79; H, 6.12; N, 5.52.

EXAMPLE 4

4,5-Dimethoxy-7-aminoethylindane

To a slurry of 15.0 g (0.395 mole) of LiAlH$_4$ and 500 ml of anhydrous ether in a 5 liter 3-necked flask fitted with a condenser, mechanical stirrer and dropping funnel was added 20.0 g (0.084 mole) of 4,5-dimethoxy-7-nitrovinylindane dissolved in 2 liters of ether. The addition was made over a period of about 4 hours while refluxing the ether slurry. When the addition was completed, refluxing was continued for an additional 1 to 2 hours. After the addition of 20 g of diatomaceous earth and then 70 ml of water slowly, dropwise, with cooling in an ice bath, the supernatant ether was decanted, the salts were washed with fresh ether several times followed by decantation and finally filtration. The solvent was removed by distillation and more thoroughly on a rotary evaporator. Cooling in an ice bath gave 15.91 g (90%) of 4,5-dimethoxy-7-aminoethylindane as a slightly yellow solid, m.p., 45°–48°C. High vacuum distillation gave an analytical sample. Anal. Calcd. for $C_{13}H_{19}NO_2$: C, 70.55; H, 8.65; N, 6.32. Found: C, 70.22; H, 8.49; N, 6.18.

EXAMPLE 5

7,8-Dimethoxy-cyclopentano [f]1,2,3,4-tetrahydroisoquinoline Hydrochloride

To 11.1 ml of formalin in a round bottom flask heated at 60°–70°C and magnetically stirred was added 10.95 g (0.049 mole) of 4,5-dimethoxy-7-aminoethylindane (dissolved in 22 ml of methanol) rapidly dropwise. After heating 50 min., the solvent was thoroughly removed on a rotary evaporator. The ir spectrum showed absence of primary amine stretching vibrations at 3190, 3300, 3370 with a weakening in intensity of the peak at 1605 cm$^{-1}$. The N-methylidene-4,5-dimethoxy-7-(2-aminoethyl)indane was dissolved in 55 ml of 23% HCl and heated on a water bath with stirring at 50°–60°C for 30 minutes. The water-acid solvent was removed on the evaporator and the residue was dried overnight in a vacuum oven giving a hard solid which yielded 11.14 g (84.1%) of 7,8-dimethoxy-cyclopentano [f]1,2,3,4-tetrahydroisoquinoline when crystallized from acetonitrile- absolute alcohol, m.p. 232°–235°C dec. Anal. Calcd. for $C_{14}H_{20}NO_2Cl$: C, 62.33; H, 7.47; N, 5.19; Cl, 13.14. Found: C, 62.58; H, 7.36; N. 5.33; Cl, 13.29.

EXAMPLE 6

4,5-Dimethoxy-6-indanaldehyde

The 4,5-dimethoxy-6-indanaldehyde was obtained by high vacuum (20–50$\mu$) fractional distillation of the mixture of aldehydes remaining after repeated crystallization and filtering off of the 7-aldehyde in Example 2. The 6-aldehyde distilled as a pure substance in the first fractions followed by a mixture of the aldehydes and finally the pure 7-aldehyde. The 4,5-dimethoxy-6-indanaldehyde was a liquid at room temperature but crystallized when refrigerated. An approximate m.p. (11°C) was obtained from the temperature of a mixture of the solid in equilibrium with the liquid. Anal. Calcd. for $C_{12}H_{14}O_3$: C, 69.88; H, 6.84. Found: C, 70.13; H, 6.87.

EXAMPLE 7

4,5-Dimethoxy-6-nitrovinylindane

In a 2 liter 3-necked flask fitted with a condenser and thermometer and magnetically stirred, 126.7 g (0.613 mole) of 4,5-dimethoxy-6-indanaldehyde, 29.3 g (0.380 mole) of ammonium acetate, 127 ml (2.82 mole) of nitromethane and 390 ml of acetic acid were heated at 112°C for 45 minutes. After cooling in the refrigerator and scratching with a glass rod the solution crystallized. After filtering and washing with cold acetic acid the product was dried under vacuum overnight and recrystallized from methanol yielding 104.4 g (68%) of 4,5-dimethoxy-6-nitrovinylindane as yellow needles, m.p. 103.5°–104.5°C. Anal. Calcd. for $C_{13}H_{15}NO_4$: C, 62.64; H, 6.06; N, 5.62. Found: C, 62.45; H, 6.17; N, 5.84.

EXAMPLE 8

4,5-Dimethoxy-6-aminoethylindane

To 9.2 g (0.242 mole) $LiAlH_4$ in 400 ml of anhydrous ether was added 12.17 g (0.048 mole) of 4,5-dimethoxy-6-nitrovinylindane in 1 liter of anhydrous ether dropwise over a period of 4 hours while refluxing; this was followed by refluxing for a further 2 hours. After adding 15 g of diatomaceous earth and decomposing excess $LiAlH_4$ with 40 ml of $H_2O$ (while cooling in an ice bath), the ether was decanted and the salts were washed twice with ether followed by decantation and finally filtering. The ether was removed by distillation and the 4,5-dimethoxy-6-aminoethylindane was distilled yielding 7.42 g (68%), b.p. 101°–103°C (75μ). Anal. Calcd. for $C_{13}H_{19}NO_2$: C, 70.55; H, 8.65; N, 6.32. Found: C, 70.68; H, 8.71; N, 6.35.

EXAMPLE 9

5,6-Dimethoxy-cyclopentano[j]1,2,3,4-tetrahydroisoquinoline Hydrochloride

To 7.42 ml of formalin in a 100 ml boiling flask was added dropwise 7.42 g (0.033 mole) of 4,5-dimethoxy-6-aminoethylindane in 15 ml of methanol with magnetic stirring and warming. After heating at 70°–75°C for 45 minutes, the mixture was rinsed into a separatory funnel with 3 × 50 ml of benzene. The benzene layer was washed with 3 × 100 ml of water and then the benzene was thoroughly removed on the evaporator. The ir spectrum showed absence of NH stretching and weakening of intensity of the band at 1576 cm$^{-1}$. The N-methylidene-4,5-dimethoxy-6-(2-aminoethyl)indane weighed 8.72 g and was dissolved in 39 ml of 23% HCl followed by heating at 50°–60°C for 30 minutes. The aqueous acid was removed on the rotary evaporator yielding an oily, viscous substance which was dried in a vacuum oven in the presence of $P_2O_5$. A tacky hygroscopic solid was obtained which was crystallized from ether-ethanol giving fine needles, m.p. 215.5°–216.5°C. Further experimentation showed acetonitrile-ethanol to be a better recrystallization solvent. Anal. Calcd. for $C_{14}H_{20}NO_2Cl$: C, 62.33; H, 7.47; N, 5.19; Cl, 13.14. Found: C, 62.47; H, 7.33; N, 5.15; Cl, 13.36.

The foregoing detailed description has been given for clearness of understanding only, and no unnecessary limitations should be understood therefrom, as modifications will be obvious to those skilled in the art.

What is claimed is:

1. A compound of the formula

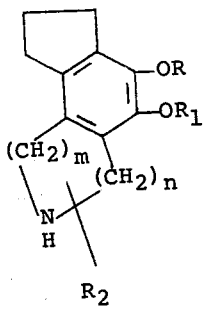

wherein R and $R_1$ are the same or different lower alkyl groups having one to six carbon atoms, $R_2$ is hydrogen or a lower alkyl group having one to six carbon atoms, $m$ is 1 or 2, $n$ is 1 or 2 and $m + n$ equals 3, and nontoxic acid addition salts thereof.

2. A compound according to claim 1 in which $m$ is 1 and $n$ is 2.

3. A compound according to claim 1 in which $m$ is 2 and $n$ is 1.

4. A compound according to claim 2 in which R and $R_1$ are methyl and $R_2$ is hydrogen.

5. A compound according to claim 3 in which R and $R_1$ are methyl and $R_2$ is hydrogen.

6. The process which comprises the steps of reacting a compound of the formula

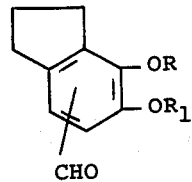

with a compound of the formula $R_2CH_2NO_2$ in glacial acetic acid in the presence of ammonium acetate to produce a compound of the formula

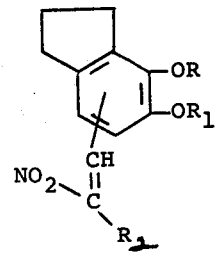

reacting said compound with lithium aluminum hydride to produce a compound of the formula

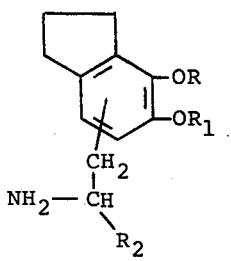

reacting said compound with formaldehyde to produce a compound of the formula

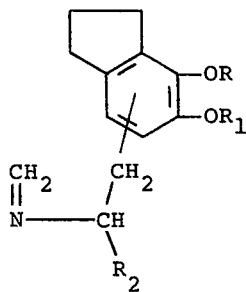

and then cyclizing said compound by reacting the compound with hydrochloric acid to produce a compound of the formula

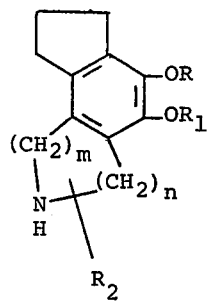

wherein R and $R_1$ are the same or different alkyl groups having one to six carbon atoms, $R_2$ is hydrogen or a alkyl group having one to six carbon atoms, $m$ is 1 or 2, $n$ is 1 or 2 and $m + n$ equals 3, and if desired converting said compound to an acid addition salt.

7. The process which comprises the step of contacting a compound of the formula

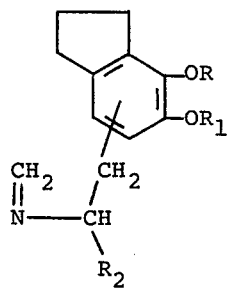

with aqueous acid to cyclize the compound and produce a compound of the formula

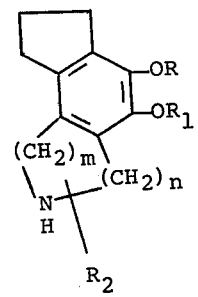

wherein R and $R_1$ are the same or different alkyl groups having one to six carbon atoms. $R_2$ is hydrogen or a alkyl group having one to six carbon atoms, $m$ is 1 or 2, $n$ is 1 or 2 and $m + n$ equals 3.

8. The process which comprises the step of contacting a compound of the formula

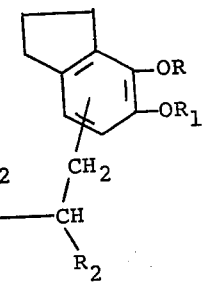

with hydrochloric acid to cyclize the compound and produce a compound of the formula

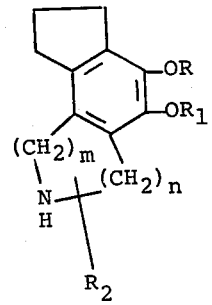

wherein R and $R_1$ are the same or different lower alkyl groups having one to six carbon atoms, $R_2$ is hydrogen or lower alkyl group having one to six carbon atoms, $m$ is 1 or 2, $n$ is 1 or 2 and $m + n$ equals 3.

9. The process of claim 8 in which R and $R_1$ are methyl and $R_2$ is hydrogen.

* * * * *

UNITED STATES PATENT AND TRADEMARK OFFICE
CERTIFICATE OF CORRECTION

PATENT NO. : 3,963,723
DATED : June 15, 1976
INVENTOR(S) : Ian W. Mathison et al.

It is certified that error appears in the above—identified patent and that said Letters Patent are hereby corrected as shown below:

Column 1, line 36, change "when" to --When--; column 3, line 28, place a comma (,) before "aluminum"; column 10, line 10, change "5.52" to --5.53--; column 11, line 46, change "[j]" to --[h]--.

Signed and Sealed this

Thirty-first Day of August 1976

[SEAL]

Attest:

RUTH C. MASON
Attesting Officer

C. MARSHALL DANN
Commissioner of Patents and Trademarks